United States Patent
Cewers

(10) Patent No.: US 10,500,367 B2
(45) Date of Patent: Dec. 10, 2019

(54) VALVE FOR CONTROLLING A FLOW

(71) Applicant: FAS Medic SA, Oron (CH)

(72) Inventor: Göran Cewers, Limhamn (SE)

(73) Assignee: FAS Medic SA, Oron (CH)

( * ) Notice: Subject to any disclaimer, the term of this patent is extended or adjusted under 35 U.S.C. 154(b) by 0 days.

(21) Appl. No.: 15/037,526

(22) PCT Filed: Nov. 20, 2014

(86) PCT No.: PCT/EP2014/075216
§ 371 (c)(1),
(2) Date: May 18, 2016

(87) PCT Pub. No.: WO2015/075158
PCT Pub. Date: May 28, 2015

(65) Prior Publication Data
US 2016/0279376 A1   Sep. 29, 2016

(30) Foreign Application Priority Data

Nov. 20, 2013 (SE) ...................................... 1351377

(51) Int. Cl.
| | |
|---|---|
| *F16K 15/00* | (2006.01) |
| *A61M 16/20* | (2006.01) |
| *A61M 16/08* | (2006.01) |
| *F16K 41/10* | (2006.01) |
| *F16K 1/42* | (2006.01) |
| *F16K 7/14* | (2006.01) |

(Continued)

(52) U.S. Cl.
CPC ...... *A61M 16/206* (2014.02); *A61M 16/0003* (2014.02); *A61M 16/0858* (2014.02);
(Continued)

(58) Field of Classification Search
CPC ..................... Y10T 137/7866; Y10T 137/7867
(Continued)

(56) References Cited

U.S. PATENT DOCUMENTS

| | | | |
|---|---|---|---|
| 2,877,791 A * | 3/1959 | Rich ......................... | F16K 7/17 |
| | | | 137/188 |
| 3,078,066 A * | 2/1963 | Moore ...................... | F16K 7/17 |
| | | | 137/510 |

(Continued)

FOREIGN PATENT DOCUMENTS

| | | |
|---|---|---|
| EP | 0126321 | 11/1984 |
| FR | 2861311 | 4/2005 |

(Continued)

OTHER PUBLICATIONS

International Search Report and Written Opinion issued in PCT Application No. PCT/EP2014/075216, dated Feb. 24, 2015, in 9 pages.

*Primary Examiner* — Robert K Arundale
(74) *Attorney, Agent, or Firm* — Knobbe, Martens, Olson & Bear, LLP

(57) ABSTRACT

A system and method for controlling a flow is disclosed. The system includes an inlet channel (100, 310) and an outlet channel (200, 320). The inlet channel has an inlet port at a first end configured to be connected to a patient, and a second end with an at least part-annularly shaped aperture (314). The outlet channel has an outlet port at a first end, and an aperture (313) at a second end. The system further comprises a flow channel arranged concentrically outside the at least part-annularly shaped aperture. The flow channel is in fluid connection with the outlet channel. The at least part-annularly shaped aperture of the inlet channel and the aperture of the outlet channel are separated by a seating means (312). The at least part-annularly shaped aperture of the inlet channel and the flow channel are separated by the seating means.

19 Claims, 4 Drawing Sheets

(51) Int. Cl.
   *F16K 25/00* (2006.01)
   *A61M 16/00* (2006.01)
   *F16K 1/44* (2006.01)
   *A61M 39/24* (2006.01)

(52) U.S. Cl.
   CPC ............. *A61M 16/205* (2014.02); *F16K 1/42* (2013.01); *F16K 1/44* (2013.01); *F16K 7/14* (2013.01); *F16K 25/00* (2013.01); *F16K 41/10* (2013.01); *A61M 2016/0027* (2013.01); *A61M 2039/2486* (2013.01); *A61M 2205/3331* (2013.01); *A61M 2205/7518* (2013.01); *Y10T 137/7866* (2015.04)

(58) Field of Classification Search
   USPC ................... 128/205.24; 251/281, 282, 319
   See application file for complete search history.

(56) References Cited

U.S. PATENT DOCUMENTS

| | | | | |
|---|---|---|---|---|
| 3,942,547 | A | | 3/1976 | Pfitzner |
| 4,241,756 | A | * | 12/1980 | Bennett ................. A61M 16/20 137/496 |
| 4,454,893 | A | * | 6/1984 | Orchard ................. A61M 16/20 128/205.24 |
| 4,699,137 | A | * | 10/1987 | Schroeder ........... A61M 16/206 128/205.24 |
| RE32,553 | E | * | 12/1987 | Bennett ................. A61M 16/20 128/204.18 |
| 4,712,580 | A | | 12/1987 | Gilman |
| 5,694,926 | A | * | 12/1997 | DeVries ............... A61M 16/125 128/204.21 |
| 6,308,731 | B1 | * | 10/2001 | Kawasaki ................. E03C 1/12 137/526 |
| 6,371,117 | B1 | | 4/2002 | Lindqvist |
| 2003/0196658 | A1 | | 10/2003 | Ging et al. |
| 2010/0186745 | A1 | * | 7/2010 | Mashak ................ A61M 16/00 128/204.26 |
| 2011/0126837 | A1 | | 6/2011 | Winter et al. |

FOREIGN PATENT DOCUMENTS

| | | |
|---|---|---|
| WO | WO 2011/022779 | 3/2011 |
| WO | WO 2015/075158 | 5/2015 |

* cited by examiner

VALVE FOR CONTROLLING A FLOW

BACKGROUND OF THE INVENTION

Field of the Invention

The invention pertains in general to the field of valves. More particularly, the invention relates to a valve device for mechanically controlling the flow of at least one fluid through at least one channel. Even more particularly, the invention relates in some examples to expiratory valves for breathing machines like medical ventilators or mechanical ventilators.

Description of the Prior Art

It is known that when designing low pressure valves, especially in the field of gas control in medical ventilators, is it of high importance that the flow channel in the valve has low flow resistance and no or little turbulence. Moreover, it is often desirable for the design of the valve to be small and light, and that the actuator controlling the valve may be made small.

Examples of low pressure valve applications are expiration valves, patient pressure relief valves, mixer valves, and flow valves in low pressure systems.

Today, the commonest design of low pressure valves comprises a circular disc lying against the end of a tube forming a valve seat. U.S. Pat. No. 5,127,400 discloses an example of such a design. The drawbacks of such a design are the complexity of the flow channel, which causes turbulence and cleaning issues. Moreover, the entire circular disc is exposed to a pressure, while the flow only depends on the outer edge of the disc. Thus an unnecessarily strong, heavy and expensive actuator is needed to control this type of valve.

U.S. Pat. No. 3,942,547 discloses a valve for directing flow of breath to and from a patient has a first port adapted to be connected to a source of breath, a second port adapted to be connected to a patient and first obturating means in the form of a diaphragm for controlling flow between the first and second ports. A second obturating means formed by a further diaphragm controls flow from the second port through the passage.

The diaphragm that controls flow between the chamber and the passage will prevent a flow there between when the diaphragm engages with concentric circular rims. This arrangement results in the elimination of noisy valve-diaphragm vibration, especially at low expiratory gas flows and to increase the effectiveness of the seat. Hence, there is no disclosure of how to obtain a more stable valve with an improved control of the opening and closing by a small and less forceful actuator.

U.S. Pat. No. 4,712,580 discloses an exhalation valve assembly for use in a volume ventilator circuit. By arranging a concentric ring support structure concentrically in the gas inlet conduit a diaphragm may be used to selectively close off the gas inlet conduit from allowing a full flow, to a reduced flow, and to prevent a flow.

Hence, there is no disclosure of how to obtain a more stable valve with an improved control of the opening and closing by a small and less forceful actuator.

Hence, an improved valve would be advantageous and, in particular an actuator-controlled valve which can be controlled using a smaller and less forceful actuator. This would improve the control of the closing and opening, improve the cost-effectiveness, and/or fulfilling the above-mentioned criteria, of a small and light actuator-controlled valve having low flow resistance and no or little turbulence.

SUMMARY OF THE DISCLOSURE

Accordingly, examples of the present invention preferably seek to mitigate, alleviate or eliminate one or more deficiencies, disadvantages or issues in the art, such as the above-identified, singly or in any combination by providing a device and a method, for controlling a flow through a valve, according to the appended patent claims.

According to one aspect of the disclosure, a valve for a medical ventilator is disclosed. The valve comprises an inlet channel and an outlet channel, wherein the inlet channel has an inlet port at a first end configured to be connected to a patient, and a second end with an at least part-annularly shaped aperture. The outlet channel has an outlet port at a first end, and an aperture at a second end. A flow channel is arranged concentrically outside the at least part-annularly shaped aperture, and the flow channel is in fluid communication with the outlet channel. The at least part-annularly shaped aperture of the inlet channel and the aperture of the outlet channel are separated by seating means. Further, the at least part-annularly shaped aperture of the inlet channel and the flow channel are also separated by seating means.

A disc is movably arranged between a closed position abutting the seating means, and an open position for allowing a flow of a fluid from the at least part-annularly shaped aperture of the inlet channel to the flow channel, and from the at least part-annularly shaped aperture of the inlet channel to the aperture of the outlet channel.

The advantages are that when the valve is open, the membrane may divert the flow from the inlet that passes through an area between the inner valve seat and the outer valve seat. The diverted flow will flow over the seating means, such as over an inner and outer valve seat, and lose energy and thereby reduce the pressure. Thus the pressure drop will be lower compared to a conventional low pressure valve which comprises a circular membrane lying against the end of a single tube forming a valve seat, for the same circumference. The reason is that the disclosed valve has a longer edge, such as the sum of an inner and outer outer valve seats, compared to a conventional low pressure valve were the edge is only the same as the circumference of its single valve seat.

Further the flow area working against the membrane of the disclosed low pressure valve is the flow area of the at least part-annularly shaped aperture, such as an area between an inner and an outer coaxially arranged valve seats. This area is smaller than for a conventional low pressure valve, having the same circumference. For a conventional low pressure valve, the flow area working against the membrane is the total area of the single tube.

Thus, the disclosed valve will require a much lower force applied by an actuator to the disc and membrane to close the valve than for a conventional low pressure valve. The reason is that the force is equal to the area times the pressure. If both the pressure and the area are smaller, then the force needed to close the valve will be smaller compared to a similar sized conventional low pressure valve.

The valve may also have improved stabilization properties, as the feedback on the inlet side is small due to the decreased area between the seating means at each side of the at least part-annularly shaped aperture of the inlet channel. At the outlet side, the feedback is reduced as, in some of the examples, the disc is effected at both sides.

According to another aspect of the disclosure, a method of stabilizing a valve id disclosed. The method comprising arranging a disc to be movable between a closed position abutting seating means, and an open position allowing a flow of a fluid from an at least part-annularly shaped aperture of an inlet channel to a flow channel, in fluid connection to an outlet channel, and from the at least part-annularly shaped aperture of the inlet channel to an aperture of the outlet channel.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the companying drawings, in which.

DESCRIPTION OF THE PREFERRED EXAMPLES

Figure 1:
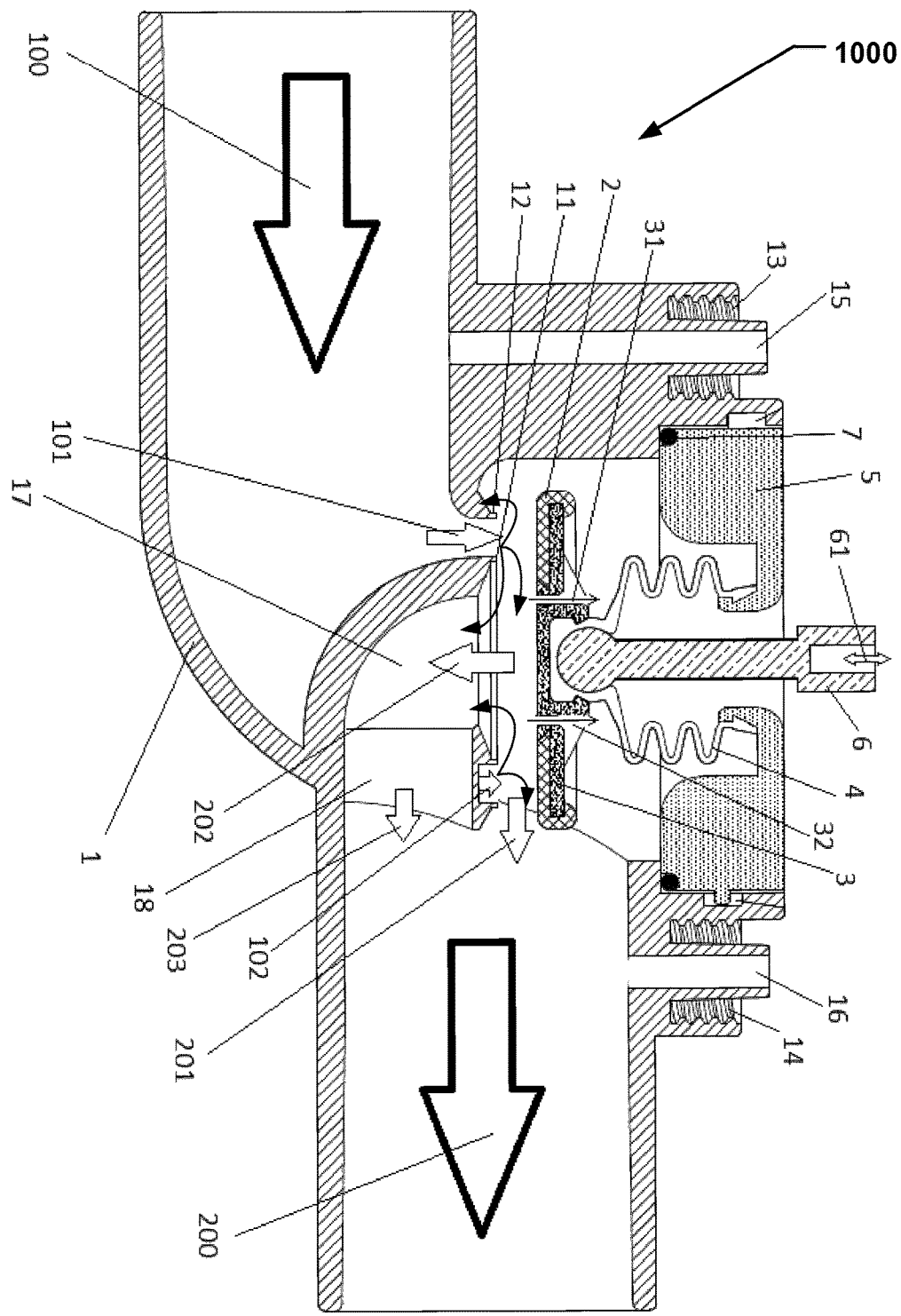
FIG. 1 is illustrating an exemplary configuration of a double edge valve.

Specific examples of the disclosure will now be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art. The terminology used in the detailed description of the examples illustrated in the accompanying drawings is not intended to be limiting of the disclosure. In the drawings, like numbers refer to like elements.

The following description focuses on a valve to control a flow of a fluid through a flow channel. In particular the valve may be used in breathing machines or medical ventilators. An example of such a valve is an expiratory valve. However, it will be appreciated that the disclosure is not limited to this application but may be applied to many other mechanical valves to control a flow.

FIG. 1 illustrates a valve including a valve housing 1, a disc membrane 2, a disc 3, a gasket 4, a lid 5, and a shaft 6. The shaft 6 is connected to an actuator to move the shaft up and down and thereby closing and opening the valve. The actuator may be any type of suitable actuators, for example a voice coil or a piezo actuator.

In some examples, the valve is a proportional valve wherein the flow may be controlled by adjusting the distance between the disc 3 and the valve seats, such as a smaller distance between the disc and the valve seats leads to a smaller flow through the valve compared to a larger distance between the disc 3 and the valve seats.

Additionally, in some examples the flow may be controlled by the force of the actuator, such as controlling the applied force when the disc is abutting the valve seats and thereby allowing a controlled leakage depending on the inlet pressure.

Additionally, in some examples of the valve, the disc 3 and disc membrane 2 may be a diaphragm.

Additionally, in some examples of the valve an or-ring 7 may be positioned between the lid 5 and the valve housing 1.

The valve further includes a plurality of valve seats 11, 12 which are formed by two coaxially and/or concentrically arranged ends of two bent tubes. An outer vale seat 12 is formed from an end of an outer tube and an inner valve seat 11 is formed from a coaxially arranged end of an inner tube.

The outer tube of the coaxially arranged ends may be formed from a 90° bend extension of an inlet tube of the valve housing 1. The inner tube of the coaxially arranged ends may be formed from a 90° bend outlet tube 17, 18. The outlet tube is upstream connected with the inlet tube, and downstream is the outlet tube forming an outlet of the valve housing 1.

Figure 2A:
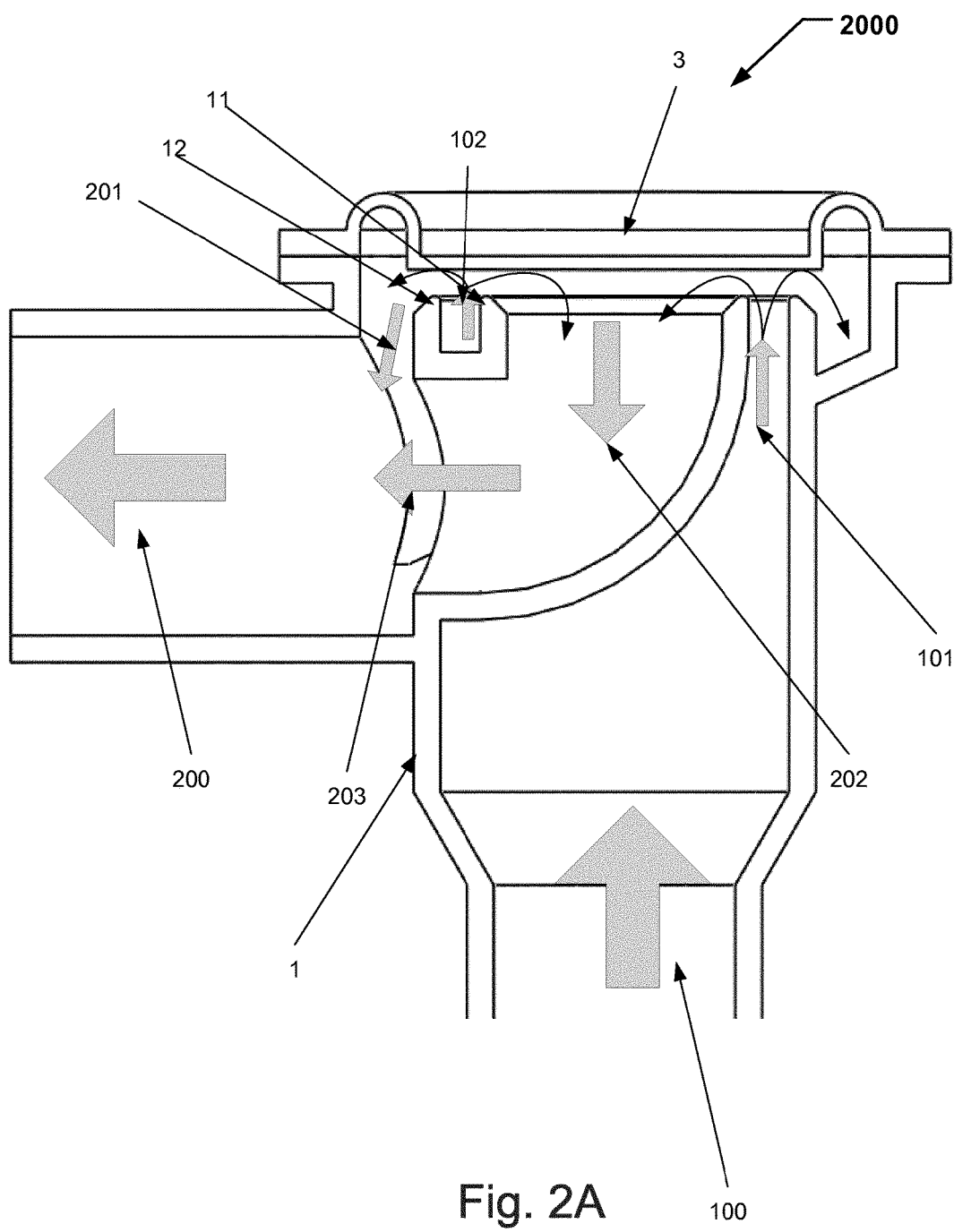
FIGS. 2A and 2B are illustrating an exemplary configuration of a double edge valve.
Figure 2B:
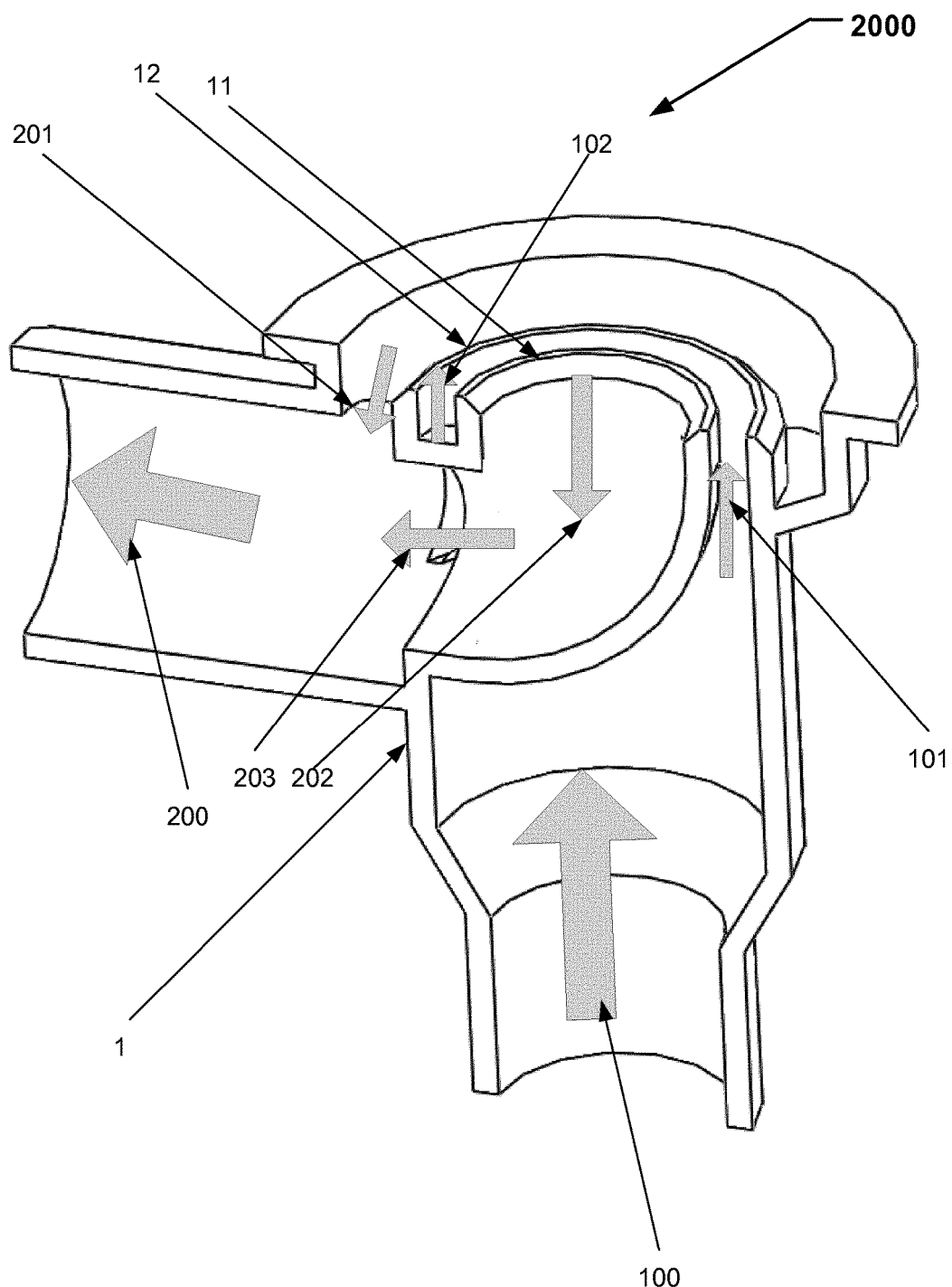

Both tubes do not necessary need to be bent 90°. Other angles are possible. It is also possible to build a combination of one straight tube and one bent, as illustrated in FIGS. 2A and 2B.

The flow path through the valve may be that a total inlet flow 100 enters the inlet tube of valve housing 1. The total inlet flow 100 is then distributed to the inlet flows 101, 102 between the circular seats 11, 12 of the two coaxial tubes.

The inlet flow is restricted by a membrane 2 on the covered disc 3. The movement of the disc 3 is controlled by the shaft 6 which is connected to a linear actuator (not shown) with movement 61 in two directions. To isolate the inside of the valve to the environment, a gasket 4 acts as a barrier between the shaft 6 and the disc 3. When disc 3 is moved from the valve seats 11, 12 by the actuator, the valve will be open and when the disc 3 moves toward the valve seats 11, 12 until the membrane 2 touches the valve seats 11, 12, the valve is closed. When the valve is open, the distributed inlet flows 101, 102 will be diverted into outlet flows. Part of the outlet flows 201 will pass outside the circular seat 12 and part of the outlet flows 202, 203 will pass inside the circular seat 11. The total outlet flow 200 is a sum of the outlet flows from these two flow paths.

Additionally, in some examples, the valve may include two pressure ports 15, 16 placed on the valve housing 1 for measuring a valve inlet pressure and a valve outlet pressure. The ports may have a Leuer-lock connection with locking threads 13, 14. The ports may then be connected to bacteria filters or tubes.

Pressure forces upstream, compared to a conventional disc valve the pressurized disc area is the area between the coaxial seats 11, 12 instead of the whole disc area inside a single circular seat. This will make the valve less sensitive for pressure variations upstream.

Pressure forces downstream, there are different sources of forces that may affect the disc 3. One is the outlet pressure effective over the area between the valve seats 11, 12. If the disc 3 has pressure equalizing flow paths 31, 32, other parts of the disc 3 may not be affected by the outlet pressure since the outlet pressure is in direct contact with the disc 3 via the outlet of the valve housing 1 and the pressure equalizing flow paths 31, 32.

Other force that may affect the disc 3 is the pressure against the gasket 4. This force is opposite to the force on the disc 3 from the outlet pressure force. The size of the gasket, and the exposed area to the outlet pressure may be chosen to bring the valve to a complete independence of the outlet pressure.

Alternatively the gasket size can be chosen to over compensate or under compensate. A bigger gasket may open the valve at high outlet pressures. A smaller gasket size may close the valve at high outlet pressures, acting like a check valve. By choosing the size of the gasket, the valve is actually capable to control flow in the opposite direction as so far described.

The valve housing described herein may be constructed using materials which are autoclavable. Alternatively, the construction material of the valve may be disposable. Alternatively, the valve may comprise parts being autoclavable combined with parts being disposable. Examples of such autoclavable materials include silicone rubber, plastics, stainless steel etc.

FIGS. 2A and 2B illustrates alternative configurations 2000 of the valve in FIG. 1. The valve illustrated in FIGS. 2A and 2B is functioning in the same way as the valve illustrated in conjunction with FIG. 1.

In FIG. 2A a disc 3 with a membrane is shown. The movement of the disc 3 may be controlled in the same way as described hereinabove in conjunction with the valve in FIG. 1. In FIG. 2B the valve is illustrated without the disc 3 with a membrane arranged above the valve seat 11, 12.

Figure 3:
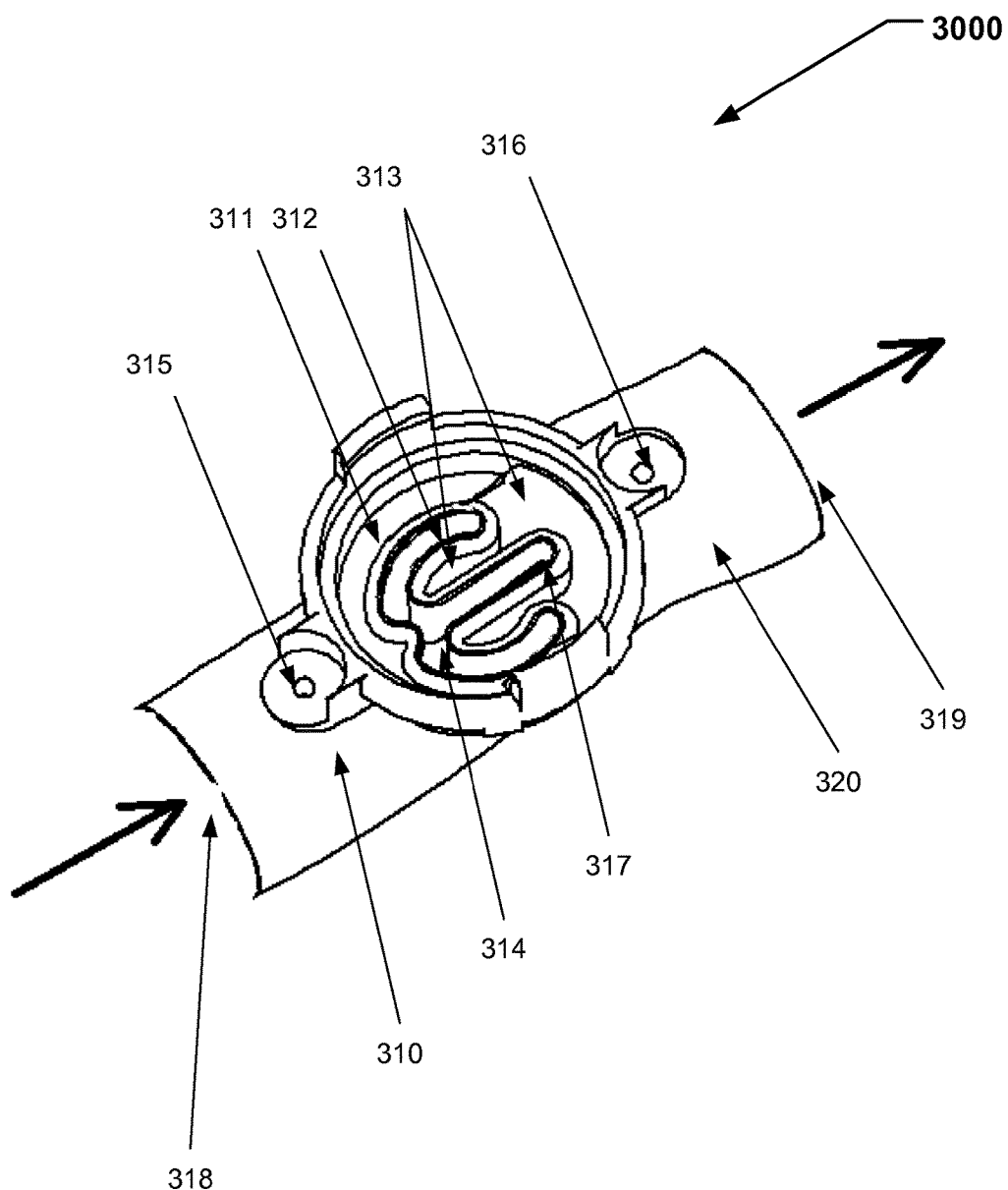
FIG. 3 is illustrating a further exemplary configuration of a double edge valve.

In FIG. 3 is an exemplary configuration 3000 of a valve in accordance with the hereinbefore disclosed principles in relation to the valve configurations of FIG. 1, and FIGS. 2A and 2B. Hence the same effects and advantages are obtained for the valve configuration 300 of FIG. 3 of for the valve configurations of FIG. 1, and FIGS. 2A and 2B.

The valve includes an inlet channel 310 and an outlet channel 320. The inlet channel 310 has an inlet port 318 at a first end configured to be connected to a patient. A second end of the inlet channel has an at least part-annularly shaped aperture 314.

The outlet channel has an outlet port 320 at a first end, and an aperture 313 at a second end. The aperture may have any suitable shape, such as circular, rectangular with a radius side, ellipsoid etc. The valve further includes a flow channel 311 arranger concentrically outside the at least part-annularly shaped aperture 314. The flow channel 311 is in fluid connection with either the outlet channel 320 or the aperture 313 of the outlet channel 320.

The at least part-annularly shaped aperture 314 of the inlet channel 310 and the aperture 313 of the outlet channel 320 are separated by a seating means 312. Also, the at least part-annularly shaped aperture 314 of inlet channel 310 and the flow channel 311 are separated by seating means 312.

In the exemplary valve configuration illustrated in FIG. 3, the seating means 312 is a continuous seating means arranged around the periphery of the at least part-annularly shaped aperture 314. Alternatively, the seating means 312 may be two valve seats, a first arranged between the flow channel 311 and the at least part-annular aperture 314 of the inlet channel 310, and a second valve seat arranged between the at least part-annular aperture 314 of the inlet channel 310 and the aperture 313 of the outlet channel.

A disc, not shown in FIG. 3, is movably arranged between a closed position abutting seating means 313, and an open position for allowing a flow of a fluid from the at least part-annularly shaped aperture 314 of the inlet channel 310 to the flow channel 311, and from the at least part-annularly shaped aperture 314 of the inlet channel 320 to the aperture 313 of the outlet channel 320.

The disc may be connected to an actuator to move disc up and down and thereby closing and opening the valve. The actuator may be any type of suitable actuators, for example a voice coil or a piezo actuator.

In some examples, the valve is a proportional valve wherein the flow may be controlled by adjusting the distance between the disc and the valve seats, such as a smaller distance between the disc and the valve seats leads to a smaller flow through the valve compared to a larger distance between the disc and the valve seats.

Additionally, in some examples the flow may be controlled by the force of the actuator, such as controlling the applied force when the disc is abutting the valve seats and thereby allowing a controlled leakage depending on the inlet pressure.

Additionally, in some examples, the valve may include two pressure ports 315, 316 placed on the valve for measuring a valve inlet pressure and a valve outlet pressure. The ports may have a Leuer-lock connection with locking threads 313, 314. The ports may then be connected to bacteria filters or tubes.

In some examples, the at least part-annular aperture 314 may have a tongue 317. The shape of the at least part-annular aperture 314 may therefore be compared to an E-shaped aperture. With this configuration the length of the seating means 313 will be longer, hence the pressure drop will be lower. At the same time this will have a small effect on the size of the area of the at least part-annular aperture 314 compared to an at least part-annular aperture without the tongue 317.

The principle of the function of the different parts of the described device may be regarded as steps for a method to mechanically control a flow in a flow channel, such as a flow channel of a medical ventilator.

As will be appreciated by one of skill in the art, the present disclosure may be embodied as device, system or method.

While several examples of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

The invention claimed is:

1. A valve comprising:
   an inlet channel and an outlet channel;
   said outlet channel has an outlet port at a first end, and an aperture at a second end;
   said inlet channel has an inlet port at a first end, and a second end with an aperture, said aperture being at least part-annularly shaped, wherein said aperture of said inlet channel is concentrically or co-axially arranged surrounding said aperture of said outlet channel;
   a flow channel is arranged concentrically outside said aperture of said inlet channel, and said flow channel is in fluid communication with said outlet channel;
   said aperture of said inlet channel and said aperture of said outlet channel are separated by a seating means, and said aperture of said inlet channel and said flow channel are also separated by said seating means;

a disc is movably arranged between a closed position abutting said seating means in which fluid communication is prevented between said aperture of said inlet channel and said flow channel and between said aperture of said inlet channel and said aperture of said outlet channel, and an open position in which said aperture of said inlet channel is in fluid communication with both said flow channel and said aperture of said outlet channel;

wherein flow through the valve is controlled by an applied mechanical force to said disc.

2. The valve according to claim 1, wherein said aperture of said inlet channel is circularly shaped.

3. The valve according to claim 1, wherein said aperture of said outlet channel is circularly shaped.

4. The valve according to claim 1, wherein the valve includes two ports for connecting pressure sensors for measuring a valve inlet pressure and a valve outlet pressure.

5. The valve according to claim 4, wherein the pressure ports are configured to be connected to bacteria filters or tubes.

6. The valve according to claim 1, wherein the disc has pressure equalizing flow paths.

7. The valve according to claim 1, wherein a pressurized disc area of said disc, when in use, has the same size as an area of said aperture of said inlet channel.

8. The valve according to claim 1, further comprising a shaft connectable to an actuator for moving the shaft up and down and thereby closing and opening the valve.

9. The valve according to claim 8, further comprising a gasket which acts as a barrier between said shaft and said disc.

10. The valve according to claim 9, wherein said size of said gasket is selected to either over compensate or under compensate for an outlet pressure.

11. The valve according to claim 9, wherein a size of said gasket is selected to make said valve independent of said outlet pressure.

12. The valve according to claim 1, wherein said seating means are arranged as a continuous seating means around said aperture of said inlet channel.

13. The valve according to claim 1, wherein said seating means are two valve seats, a first valve seat is arranged to separate said aperture of said inlet channel from said flow channel, and a second valve seat is arranged to separate said aperture of said outlet channel from said aperture of said inlet channel.

14. The valve according to claim 1, wherein said first valve seat, and said second valve seat are circularly shaped.

15. The valve according to claim 1, wherein said disc is a diaphragm means.

16. A method of stabilizing a valve, comprising: arranging a disc to be movable between a closed position abutting said seating means in which fluid communication is prevented between an at least part-annularly shaped aperture of an inlet channel and a flow channel, said flow channel in fluid connection to an outlet channel, and between said at least part-annularly shaped aperture of said inlet channel and an aperture of said outlet channel, and an open position in which said at least part-annularly shaped aperture of said inlet channel is in fluid communication with both said flow channel and said aperture of said outlet channel, and controlling flow through the valve using an applied mechanical force to said disc, wherein said aperture of said inlet channel is concentrically or co-axially arranged surrounding said aperture of said outlet channel.

17. The method according to claim 16, comprising controlling an actuator for adjusting a distance between said disc and said seating means, and thereby controlling the flow through the valve.

18. The method according to claim 16, comprising applying the applied mechanical force using an actuator, and controlling the applied mechanical force applied by said actuator to allow a controlled leakage when said disc is abutting said seating means depending on the inlet pressure.

19. A valve comprising:
an inlet channel and an outlet channel;
said outlet channel has an outlet port at a first end, and an aperture at a second end;
said inlet channel has an inlet port at a first end, and a second end with an aperture, said aperture being at least part-annularly shaped, wherein said aperture of said inlet channel is concentrically or co-axially arranged surrounding said aperture of said outlet channel;
a flow channel is arranged concentrically outside said aperture of said inlet channel, and said flow channel is in fluid communication with said outlet channel;
said aperture of said inlet channel and said aperture of said outlet channel are separated by a seating means, and said aperture of said inlet channel and said flow channel are also separated by said seating means;
a disc is movably arranged between a closed position abutting said seating means in which fluid communication is prevented between said aperture of said inlet channel and said flow channel and between said aperture of said inlet channel and said aperture of said outlet channel, and an open position in which said aperture of said inlet channel is in fluid communication with both said flow channel and said aperture of said outlet channel;
wherein flow through the valve is controlled by an applied force to said disc to close the valve.

* * * * *